United States Patent
Bier et al.

(10) Patent No.: US 9,427,869 B2
(45) Date of Patent: Aug. 30, 2016

(54) MOTORIZED ASSISTANCE IN THE MOVEMENT OF A MEDICAL APPARATUS

(71) Applicants: Peter Bier, Gremsdorf (DE); Harald Mulzer, Speinshart (DE); Wolfgang Neuber, Pressath (DE); Matthias Schirbl, Freihung (DE)

(72) Inventors: Peter Bier, Gremsdorf (DE); Harald Mulzer, Speinshart (DE); Wolfgang Neuber, Pressath (DE); Matthias Schirbl, Freihung (DE)

(73) Assignee: Siemens Aktiengesellschaft, München (DE)

( * ) Notice: Subject to any disclaimer, the term of this patent is extended or adjusted under 35 U.S.C. 154(b) by 7 days.

(21) Appl. No.: 14/102,447

(22) Filed: Dec. 10, 2013

(65) Prior Publication Data
US 2014/0163734 A1    Jun. 12, 2014

(30) Foreign Application Priority Data

Dec. 11, 2012 (DE) .................. 10 2012 222 779

(51) Int. Cl.
*G05B 15/00*    (2006.01)
*B25J 9/16*    (2006.01)
*A61B 6/00*    (2006.01)

(52) U.S. Cl.
CPC ............ *B25J 9/1633* (2013.01); *A61B 6/4441* (2013.01); *A61B 6/4447* (2013.01); *A61B 6/54* (2013.01); *Y10S 901/09* (2013.01)

(58) Field of Classification Search
CPC ... G06K 9/46; G06K 2009/4666; G06T 3/40
See application file for complete search history.

(56) References Cited

U.S. PATENT DOCUMENTS

| | | | |
|---|---|---|---|
| 5,671,266 A * | 9/1997 | Linhart ............... | A61B 6/4482 378/175 |
| 2005/0100134 A1* | 5/2005 | Bauer .................. | A61B 6/4482 378/197 |
| 2007/0078534 A1* | 4/2007 | Boomgaarden ...... | A61B 6/4429 700/63 |
| 2008/0098526 A1 | 5/2008 | Doleschal et al. | |
| 2010/0007295 A1* | 1/2010 | Yang ...................... | H02P 6/085 318/400.22 |
| 2012/0106701 A1* | 5/2012 | Meek ................... | A61B 6/4476 378/62 |
| 2014/0163734 A1* | 6/2014 | Bier ...................... | B25J 9/1633 700/258 |

FOREIGN PATENT DOCUMENTS

CN    2228225 Y    5/1996
CN    1939222 A    4/2007
(Continued)

OTHER PUBLICATIONS

ATI Industrail Automation; Six Axis Force/Torque Transducer Aug. 2010.*
(Continued)

*Primary Examiner* — Ian Jen
(74) *Attorney, Agent, or Firm* — Lempia Summerfield Katz LLC

(57) ABSTRACT

An arrangement for motorized assistance in movement of manually movable components of medical apparatuses is provided. The arrangement includes at least one torque sensor that is arranged in a drivetrain of a movable component of a medical apparatus. The at least one torque sensor detects the moments occurring in the drivetrain in a stationary state and in motion. Using an evaluation unit, the torque detected by the at least one torque sensor may be compared against a predefinable first threshold value. The first threshold value is predefined according to a possible position of the movable component. The arrangement includes a drive unit, by which the drive of the drivetrain may be provided with motorized assistance when the first threshold value is exceeded.

8 Claims, 2 Drawing Sheets

(56) References Cited

FOREIGN PATENT DOCUMENTS

| | | |
|---|---|---|
| CN | 101031241 A | 9/2007 |
| CN | 102421364 A | 4/2012 |
| DE | 4237013 A1 | 5/1994 |
| DE | 4433036 A1 | 3/1996 |
| DE | 103 47 738 B4 | 1/2012 |

OTHER PUBLICATIONS

German Office Action dated Aug. 14, 2013 for corresponding German Patent Application No. DE 10 2012 222 779.2 with English translation.

Chinese Office action for related Chinese Application No. 201310671732.9, dated Jun. 16, 2015, with English Translation.

* cited by examiner

MOTORIZED ASSISTANCE IN THE MOVEMENT OF A MEDICAL APPARATUS

This application claims the benefit of DE 10 2012 222 779.2, filed on Dec. 11, 2012, which is hereby incorporated by reference in its entirety.

BACKGROUND

The present embodiments relate to an arrangement for motorized assistance in movement of manually movable components of medical apparatuses, and to an associated method.

X-ray imaging apparatuses assist a treating physician in a diagnosis and treatment of diseases of the patient. These apparatuses may have a plurality of electrically powered, movable shafts that permit the three-dimensional movement and positioning of apparatus components (e.g., an X-ray source, an X-ray detector, or a tabletop of a patient table). Since the apparatus components may have a considerable inertial mass, known X-ray imaging apparatuses make use of servo motors in order to strengthen the force applied to an apparatus component by the operator (e.g., via a handle), such that the apparatus component may be spatially moved and positioned effortlessly and without great force being applied.

DE 44 33 036 A1 describes an X-ray examination apparatus with an X-ray target device that includes an X-ray detector and an X-ray source for converting and reproducing an X-ray image, received by the X-ray detector, on a monitor, and a movable X-ray source under a patient table. The X-ray target device includes an operating handle and may be moved by the handle in at least two different spatial directions. A plurality of sensors are arranged in relation to the operating handle such that, when a force is applied to the operating handle in any desired direction of at least four possible movement directions, another group of at least two of the sensors is activated in each case.

The document DE 103 47 738 B4 describes a motor-adjustable X-ray apparatus including a C-arm that has two degrees of freedom and is adjustable with motor assistance. The X-ray apparatus includes a force pick-up device that is provided to detect a force exerted by an operator when manipulating the C-arm. The force pick-up device detects a plurality of directional components of the force and cooperates with an evaluation unit, by which, as a function of the distribution of the directional components of the force, different degrees of motor assistance of the C-arm in the two degrees of freedom may be established. In a memory unit, characteristic curves with respect to the motorized assistance of the C-arm in different degrees of freedom are stored by dividing the directional components of the force.

DE 42 37 013 A1 describes an X-ray apparatus with a force pick-up device for detecting the force applied by the user to move a positioned C-arm. To select and deselect adjustable axes of the C-arm, several keys that may be moved along with the C-arm are provided. The operator is given the impression that he is moving the X-ray apparatus with substantially smaller masses or moments of inertia. Although the provided servo-assistance to the C-arm permits adjustment with low operating forces, this smooth running of the C-arm poses the danger of an adjustment being made unintentionally.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an arrangement for motorized assistance in the movement of manually movable components of medical apparatuses, and a method for the adjustment thereof are provided.

In one embodiment, an arrangement for motorized assistance in movement of manually movable components of medical apparatuses is provided. The arrangement includes at least one torque sensor that is arranged in a drivetrain of a movable component of the medical apparatus. The torque sensor detects moments occurring in the drivetrain in a stationary state and in motion. Using an evaluation unit, the torque detected by the torque sensor may be compared against a predefinable first threshold value. The first threshold value is predefined according to a possible position of the movable component. The arrangement includes a drive unit, by which the drive of the drivetrain may be provided with motorized assistance when the first threshold value is exceeded. This advantageously permits motor-assisted movement and positioning of the movable components of the medical apparatus.

In one embodiment, the evaluation unit may be configured such that the detected torque may be compared against a predefinable second threshold value. The second threshold value is predefined according to the possible position of the movable component. The drive unit is configured such that, when the second threshold value is not reached, the motorized assistance of the drive of the drivetrain ends. The second threshold value is greater than the first threshold value. Via the second threshold value, it is thus possible to provide that the motorized assistance in the movement of a component ends when a target position of the component is reached, and no more manual force is applied to the component.

In another embodiment, the evaluation unit may be configured to compare the detected torque against a predefinable third threshold value. The third threshold value is predefined according to the possible position of the movable component. The drive unit is configured such that the movement may be stopped by motor when the third threshold value is exceeded. Via the third threshold value, it is thus advantageously possible to provide that, if a component with movement is provided with motorized assistance collides with an obstacle (e.g., with a wall or with another component of the medical apparatus), the movement may be stopped by motor.

One or more of the present embodiments provide a method for motorized assistance in the movement of manually movable components of medical apparatuses. A torque in a drivetrain is detected. The detected torque is compared against a predefinable first threshold value. The first threshold value is predefined according to the possible position of the movable component. If the detected torque exceeds the first threshold value, this leads to motorized assistance of the drive of the drivetrain.

The detected torque may be compared against a predefinable second threshold value. The second threshold value is predefined according to the possible position of the movable component. The second threshold value is greater than the first threshold value. If the second threshold value is not reached, the motorized assistance of the drive of the drivetrain is terminated.

Advantageously, the detected torque may be compared against a predefinable third threshold value. The third threshold value is predefined according to the possible position of the movable component. If the third threshold value is exceeded, the movement is stopped by motor.

One or more of the present embodiments provide a method for determining a torque with a device as described above. A change of angle of the drivetrain is determined as a result of elastic deformation. The torque is determined by multiplying the change of angle by a torsion spring constant of the drivetrain. The torsion spring constant of the drivetrain was determined beforehand by measurement. In this way, in an alternative to the use of a torque sensor, a torque occurring on the drivetrain may be advantageously calculated from the elastic deformation of the drivetrain.

DETAILED DESCRIPTION

Figure 1:
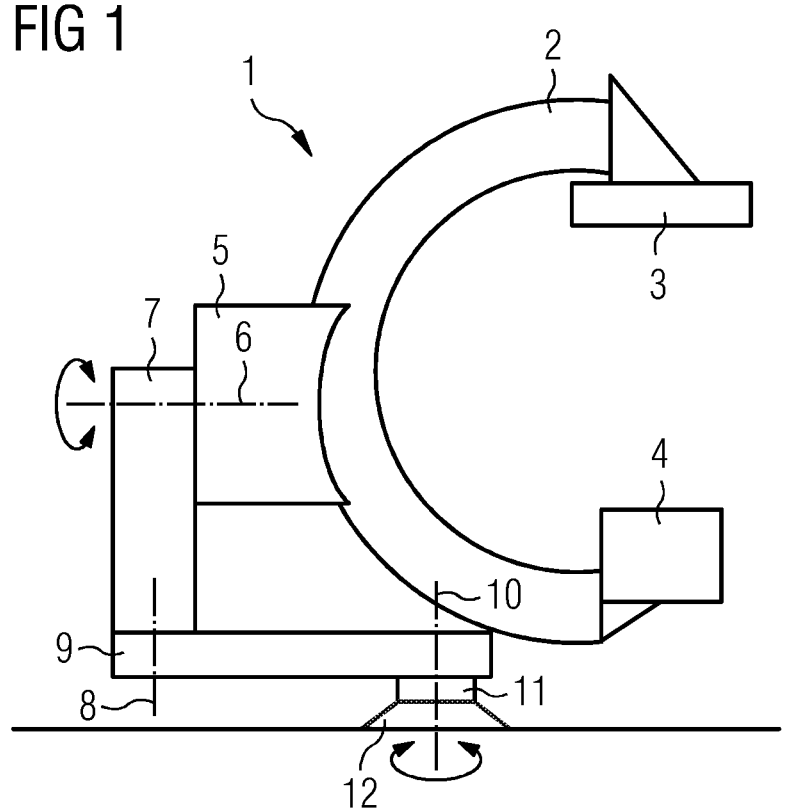
FIG. 1 shows a perspective view of one embodiment of a C-arm X-ray apparatus with a plurality of rotatable components.

FIG. 1 shows a perspective view of one embodiment of a C-arm X-ray apparatus with a plurality of rotatable components.

The C-arm X-ray apparatus 1 includes a C-arm 2 with an X-ray source 3 and an X-ray detector 4. The C-arm 2 is secured on a holder 5 that is connected to a column 7 and is rotatable about a first horizontal rotation axis 6. The column 7 is arranged on one end of a rotary arm 9 and is rotatable about a second vertical rotation axis 8. At an opposite end, the rotary arm 9 is arranged, rotatably about a third vertical rotation axis 10, on a base axle 11 that rests immovably on a floor plate 12. The rotations of the holder 5 about the first rotation axis 6, of the column 7 about the second rotation axis 8, and of the rotary arm 9 about the third rotation axis 10 may be effected manually, by motor, or manually with motorized assistance. The motorized movement is obtained via drive units (not shown). Each of the drive units includes a motor with gears and a drivetrain. To detect the torques on the individual rotation axes 6, 8, 10, torque sensors (not shown) are arranged between the drive units and the rotatable components 5, 7, 9.

Figure 2:
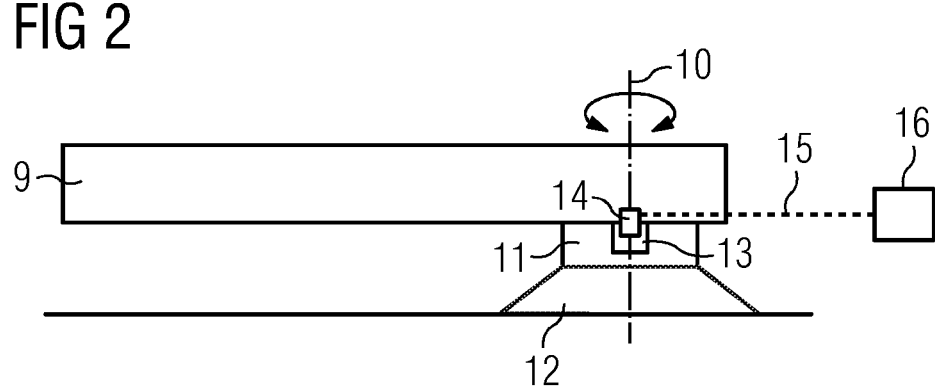
FIG. 2 shows a schematic representation of one embodiment of a rotatable component with drive unit and torque sensor.

FIG. 2 shows one embodiment of a rotatable component with drive unit and torque sensor. A rotary arm 9 of a C-arm X-ray apparatus is arranged, rotatably about a third vertical rotation axis 10, on a base axle 11 that rests immovably on a floor plate 12. The rotation of the rotary arm 9 about the third rotation axis 10 may be effected manually, by motor, or manually with motorized assistance. The motorized movement is obtained via a drive unit 13 that is arranged in the base axle 11 and includes a motor with gears and a drivetrain. The drive of the drivetrain may be provided with motorized assistance via the drive unit 13. To detect the torque on the third rotation axis 10, a torque sensor 14 is arranged between the drive unit 13 and the rotary arm 9 on the drivetrain of the drive unit 13. The torque sensor 14 detects the torques on the third rotation axis 10 and therefore the moments occurring on the drivetrain. The torques are fed via a data interface 15 to an evaluation unit 16 arranged in the C-arm X-ray apparatus.

The torque detected by the torque sensor 14 and generated, for example, by an operator applying a manual force to the movable rotary arm 9 may be compared against a predefinable first threshold value by the evaluation unit 16. The first threshold value is predefined according to the possible position of the movable component. If the first threshold value is exceeded, the drive of the drivetrain is provided with motorized assistance by the drive unit 13. The torque continuously detected by the torque sensor 14 during the movement of the rotary arm 9 is compared against a predefinable second threshold value. The second threshold value is predefined according to the possible position of the movable component. If the second threshold value is not reached, the motorized assistance of the drive of the drivetrain by the drive unit 13 ends. The second threshold value is greater than the first threshold value. By way of the second threshold value, it is thus possible to provide that the motorized assistance in the movement of the rotary arm 9 ends when the rotary arm 9 has reached a target position, and no more manual force is applied to the rotary arm 9 by the operator.

The continuously detected torques are compared against a predefinable third threshold value. The third threshold value is predefined according to the possible position of the movable component. If the third threshold value is exceeded, the movement is stopped by motor by the drive unit 13. By way of the third threshold value, it is thus possible to provide that, if the rotary arm 9 having movement that is provided with motorized assistance collides with an obstacle (e.g., with a wall or with another component of the medical apparatus), the motorized assistance of the movement is terminated by the drive unit 13, and the movement is stopped.

Figure 3:
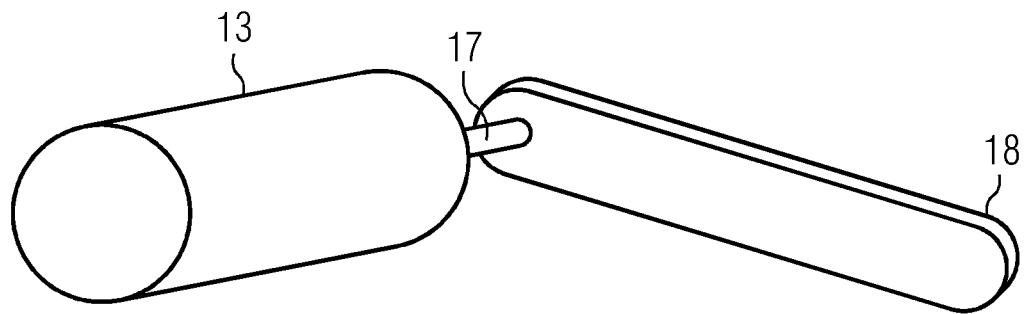
FIG. 3 shows one embodiment of an arrangement for measuring a torque by determining a change of angle of a drivetrain of a rotatable component upon torsion of the drivetrain.

FIG. 3 shows one embodiment of an arrangement for measuring a torque by determining a change of angle of a drivetrain of a rotatable component upon torsion of the drivetrain. By way of a drivetrain 17 of a drive unit 13, a movable component 18 of a C-arm may be moved manually or with motorized assistance by the drive unit 13. The drive unit 13 has a torsion spring constant that describes torsional stiffness and may be determined by metrology. By way of the drivetrain 17, a torque is transmitted to the movable component 18. The effect of a force on the movable component 18 (e.g., in the event of the movable component 18 colliding with an obstacle) leads to an elastic deformation of the force-transmitting or moment-transmitting elements in the drive unit 13 and to a change of angle of the drivetrain 17. If the change of angle of the drivetrain 17 is detected, the torque transmitted to the movable component 18 via the drivetrain 17 may be determined by multiplying the change of angle by a torsion spring constant of the drivetrain 17. The torsion spring constant of the drivetrain 17 was determined beforehand by measurement.

Figure 4:
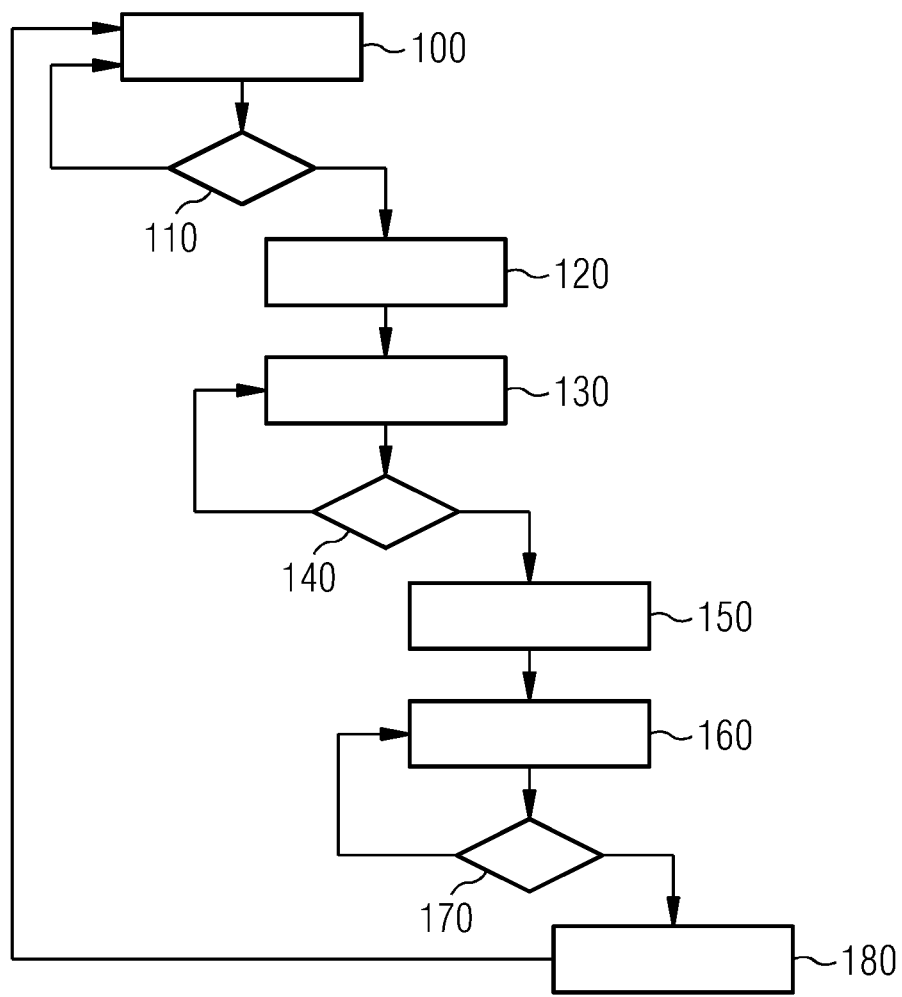
FIG. 4 shows a flowchart of one embodiment of a method for motorized assistance in the movement of manually movable components.

FIG. 4 shows a flowchart of one embodiment of a method for motorized assistance in the movement of manually movable components. In act 100, a torque occurring in a drivetrain is detected. In act 110, the detected torque is compared against a predefinable, position-dependent first threshold value. If the first threshold value is exceeded, motorized assistance is provided to the drive of the drivetrain in act 120, and the method is continued with act 130. If the comparison in act 110 shows that the first threshold value is not exceeded, the method is continued with act 100.

In act 130, the torque occurring in the drivetrain is detected again. In act 140, the detected torque is compared against a predefinable, position-dependent second threshold value that is greater than the first threshold value. If the second threshold value is not reached, the motorized assistance of the drive of the drivetrain is terminated in act 150, and the method is continued with act 160. If the comparison in act 140 shows that the second threshold value is exceeded, the method is continued with act 130.

In act 160, the torque occurring in the drivetrain is detected. In act 170, the detected torque is compared against a predefinable, position-dependent third threshold value. If the third threshold value is exceeded, the movement of the drive of the drivetrain is stopped by motor in act 180, and the method is continued with act 100. If the comparison in act 170 shows that the third threshold value is not exceeded, the method is continued with act 160.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An arrangement for motorized assistance in movement of manually movable components of medical apparatuses, the arrangement comprising:
    at least one torque sensor that is arranged in a drivetrain;
    an evaluation unit configured to compare a torque detected by the at least one torque sensor against a first threshold value that is predefinable and position-dependent in that the first threshold value is predefined according to a possible position of a movable component; and
    a drive unit operable to provide drive of the drivetrain with motorized assistance when the first threshold value is exceeded.

2. The arrangement of claim 1, wherein the evaluation unit is configured to compare the detected torque against a second threshold value that is predefinable and position-dependent,
    wherein the drive unit is configured to end the motorized assistance of the drive of the drivetrain when the second threshold value is not reached, and
    wherein the second threshold value is greater than the first threshold value.

3. The arrangement of claim 2, wherein the evaluation unit is configured to compare the detected torque against a third threshold value that is predefinable and position-dependent, and
    wherein the drive unit is configured to stop the movement by the drive unit when the third threshold value is exceeded.

4. The arrangement of claim 1, wherein the evaluation unit is configured to compare the detected torque against a second threshold value that is predefinable and position-dependent, and
    wherein the drive unit is configured to stop the movement by the drive unit when the second threshold value is exceeded.

5. A method for motorized assistance in movement of manually movable components of medical apparatuses, the method comprising:
    detecting a torque in a drivetrain;
    comparing the detected torque against a first threshold value that is predefinable and position-dependent in that the first threshold value is predefined according to a possible position of a movable component; and
    providing motorized assistance of drive of the drivetrain when the first threshold value is exceeded.

6. The method of claim 5, further comprising:
    comparing the detected torque against a second threshold value that is predefinable and position-dependent, wherein the second threshold value is greater than the first threshold value; and
    terminating the motorized assistance of the drive of the drivetrain when the second threshold value is not reached.

7. The method of claim 6, further comprising:
    comparing the detected torque against a third threshold value that is predefinable and position-dependent; and
    motorized stopping the movement when the third threshold value is exceeded.

8. The method of claim 5, further comprising:
    comparing the detected torque against a second threshold value that is predefinable and position-dependent; and
    motorized stopping the movement when the second threshold value is exceeded.

* * * * *